United States Patent [19]

Eriksson

[11] 4,411,915
[45] Oct. 25, 1983

[54] HEME-IRON-ENRICHED AMINO ACID AND A PROCESS FOR THE PREPARATION OF HEME-IRON-ENRICHED AMINO ACID

[76] Inventor: Caj Eriksson, Näverlursvägen 1, 435 00 Mölnlycke, Sweden

[21] Appl. No.: 255,218

[22] Filed: Apr. 18, 1981

[51] Int. Cl.$^3$ .......................... A23J 1/06; C12P 21/06
[52] U.S. Cl. ....................................... 426/32; 426/656; 435/69; 435/269; 260/112 B; 260/115
[58] Field of Search .................... 426/32, 656; 435/69, 435/269; 260/112 B, 115

[56] References Cited

U.S. PATENT DOCUMENTS

| | | | |
|---|---|---|---|
| 2,912,359 | 11/1959 | Anigstein et al. | 435/69 X |
| 2,958,630 | 11/1960 | Keil et al. | 426/32 X |
| 4,098,780 | 7/1978 | Lindroos | 426/647 X |
| 4,262,022 | 4/1981 | Christensen et al. | 426/32 |
| 4,330,463 | 5/1982 | Luijerink | 426/647 X |

FOREIGN PATENT DOCUMENTS 2037188  7/1969  Fed. Rep. of Germany ... 260/112 B

Primary Examiner—Robert A. Yoncoskie
Attorney, Agent, or Firm—Abelman, Frayne & Rezac

[57] ABSTRACT

There is disclosed heme-iron-enriched amino acid preparation consisting of aggregates of heme-protein fragments with heme bonded to histidine groups present in the fragment and a method for preparing this amino acid preparation from heme-proteins, especially hemoglobin. The heme-protein in a manner known per se at first is hemolyzed and denaturated and subsequently split with the aid of proteolytic enzymes to the formation of one heme-iron-enriched and one fraction which does not contain heme-iron and separation of these fractions from each other. The amino acid preparation is suitable for iron enrichment of for instance foodstuffs and for use in pharmaceutical iron preparations.

12 Claims, 1 Drawing Figure

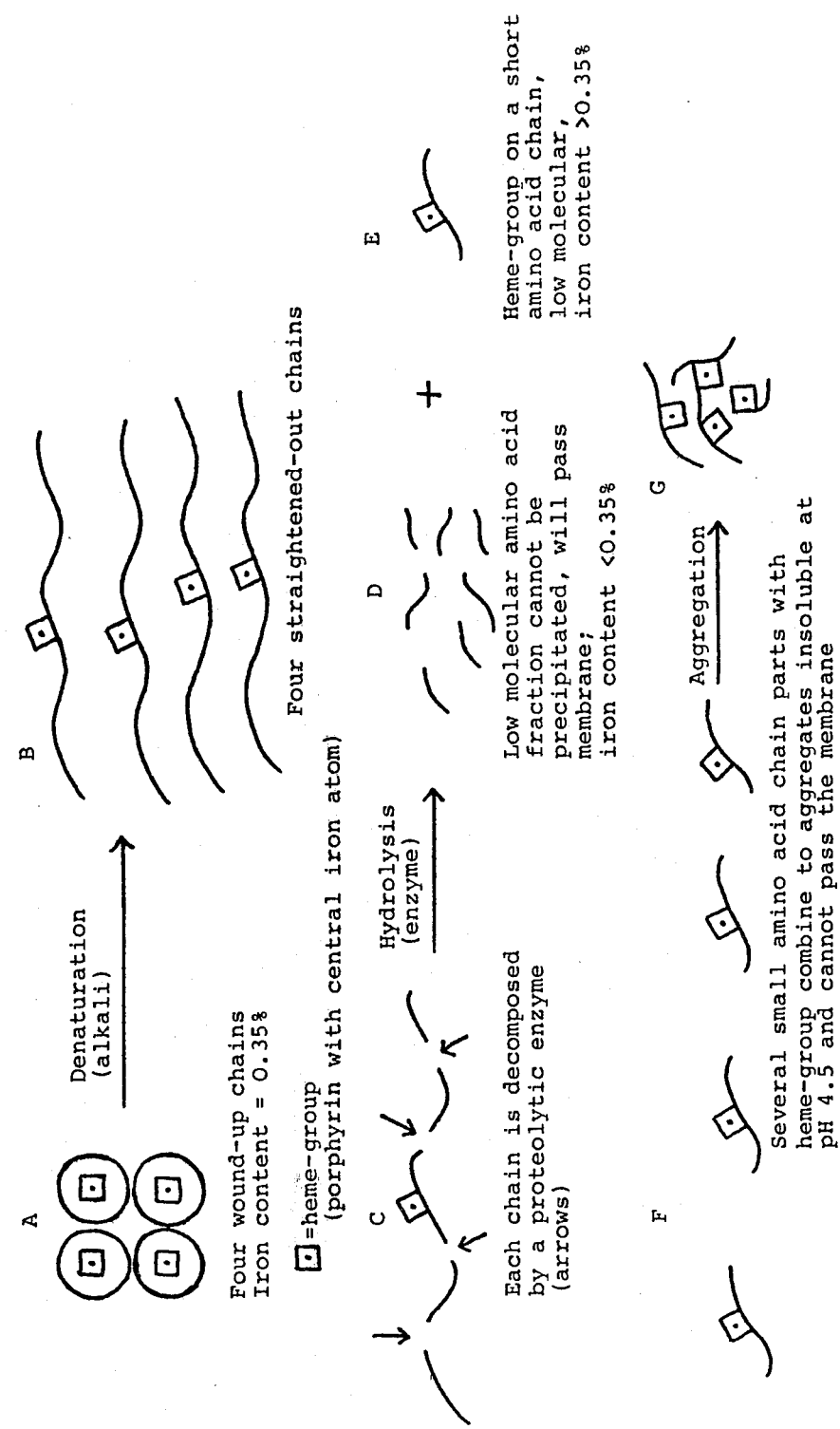
FIGURE 1. PRINCIPLES FOR PREPARING HEME-IRON-ENRICHED PRODUCTS

HEME-IRON-ENRICHED AMINO ACID AND A PROCESS FOR THE PREPARATION OF HEME-IRON-ENRICHED AMINO ACID

The present invention relates to a heme-iron-enriched amino acid preparation and a process for the preparation of heme-iron-enriched amino acid preparations from heme-proteins, especially hemoglobin.

Hemoglobin in animal as well as human blood and also other natural hemoproteins consists of a great number of amino acids which are chemically bonded to each other in long chains. Certain heme-proteins, e.g. peroxidase in plants, also contain carbohydrates. Hemoglobin contains four amino acid chains. A special group, a heme-group, is connected to each chain. This heme-group consists of porphyrin to which a central iron atom is bonded. Thus, each hemoglobin molecule consists of totally four amino acid chains with totally four heme-groups containing together four iron atoms. This heme gives the blood its oxygen-transporting ability. The heme also contributes to the colour of blood. Heme is bonded at the amino acid chain by a bonding between on the one side the iron atom of the heme and on the other to a special amino acid in the chain. There are several histidine groups in each chain but only one of them is thus used for the heme-bonding.

It is known that the iron which is administrated to the body in the form of heme, essentially from hemoglobin and myoglobin, in certain cases is better utilized than the other forms of iron, e.g. ferrum reductum or different iron salts which are the usual forms of iron for enrichment of foodstuffs, e.g. flour, drinks or for use in pharmaceutical iron preparations. The need for iron enrichment, e.g. in certain foodstuffs such as bread, is well documented.

The heme-iron is absorbed in the human body by another mechanism than other types of iron; there is a distinction between the absorption via the so-called heme-iron pool and the non-heme-iron pool. This partly explains why the utilization of heme-iron in the body is influenced to a lesser extent by other foodstuff components than other forms of iron. Thus, the heme-iron utilization is not influenced in a negative direction by for instance phytinic acid and its salts which are present in cereals and cereal products, or tannic acid in for instance tea, phosphate or other components in eggs, which is the case for other iron forms.

Other forms can, especially in high doses, give different side-reactions in man. The most important advantages with heme-iron in diet contexts would thus be its inherent natural properties including independence of other foodstuff components in the utilization in the body and lesser side effects. An important condition for correct resorption of heme is, however, that it is bonded to a suitable carrier. Iron in heme is thus very poorly utilized if the heme first is separated from protein and administrated separately. This leads to the conclusion that the amino acid chain to which the heme originally is bonded should have a positive influence in this respect.

The hemoglobin molecule consists, calculated on the weight, predominantly of amino acids. In 1000 mgs of hemoglobin the amino acids are together about 960 mgs and heme only 40 mgs, which is equivalent with 3.5 mgs of iron, viz. only 4% by weight heme and 0.35% by weight of iron resp.

This means that a great amount of amino acids automatically must be administrated to the body in relation to the amount of iron if hemoglobin is utilized as a source of iron. If for instance the daily need of iron (15 mgs) would be administrated in the form of hemoglobin simultaneously 4.2 gs of amino acids (7% of the daily need of protein) would have to be consumed. A therapeutical dosis of 100 mgs of iron daily would mean an extra addition of about 28 gs of amino acids, which corresponds to nearly half of the daily need of protein. It is unrealistic to administrate such great amounts of amino acids above the amount of protein which is administrated through the food.

If hemoglobin would be used for iron-enrichment of foodstuffs all the protein simultaneously administrated would correspondingly harmfully influence the technical properties of the foodstuff and possibly also its nutritional value. Accordingly, there is a need for a heme-iron product with the following properties:
- a higher heme content (and accordingly a higher iron content) than hemoglobin
- the heme is bonded in a similar manner as in hemoglobin
- good solubility properties for admixture in all types of foodstuffs and pharmaceutical preparations.

It has now been found that these requirements are fulfilled by a heme-iron-enriched amino acid preparation prepared from heme-proteins. The preparation is characterized in that its iron content exclusively consists of the porphyrin iron of the original heme-protein bonded in this form (heme) to amino acid chains, which are considerably shorter than the amino acid chains in the original heme-protein, viz. these chains have for achievement of the enrichment been made shorter. However, these amino acid chains have dimensions which are longer than the separate short, heme-iron-containing amino acid chains which for instance has been achieved by aggregation. This will permit separation from amino acid chains which do not contain heme-iron. It is suitable that the preparation has a constant ratio between heme and iron and a porphyrin heme-iron content of at least 0.5% and preferably at the most 5%, calculated on the iron bonded to porphyrin.

The invention relates primarily to a process for the preparation of heme-iron-enriched amino acid preparations from heme-proteins, especially hemoglobin. The process is characterized in that the heme-protein in a manner known per se first is hemolyzed and denaturated and subsequently split with the aid of proteolytic enzymes to one heme-iron-enriched and one heme-iron-poor fraction and in that the heme-iron-enriched fraction is obtained by separation, the heme-iron-enriched fraction preferably being aggregated. The preparation is subsequently stabilized by heat-treatment and concentrated, preferably by drying.

The stabilization of the heme-iron-enriched fraction is made by a heat-treatment in which the enzymes are inactivated. The most common treatment is pasteurization at for instance 70° C. for 30 minutes and/or sterilization at 121° C. for 5 minutes. Pasteurization is preferably made at 60°–90° C. for 3–10 minutes but can also be made at higher temperatures, e.g. 90°–110° C. for a shorter period of time. Sterilization is preferably made at 110°–121° C. for 20–5 minutes and can also be made at a higher temperature and for a correspondingly shorter period of time. The determination of a suitable temperature and a corresponding period of time is made by routine experiments.

The invention is further elucidated with reference to the enclosed drawing on which FIG. 1A diagramatically shows a heme-protein molecule. FIG. 1B shows this molecule after denaturation. FIG. 1C shows one of the four straightened chains of denaturated protein according to FIG. 1B. FIG. 1D represents the amino acid fraction obtained after the reaction and FIG. 1E shows a heme-iron-enriched amino acid preparation according to the invention. Finally, FIG. 1F shows how several such heme-iron-enriched amino acid preparations are combined to aggregates.

As has been mentioned above a hemoglobin molecule consists of four amino acid chains, each of which contains a heme-group the iron atom of which is bonded to one of the histidin groups of the chain. These chains are in the natural condition wound up in a complex manner so that each heme-group is located within the would chain. The major part of the bondings which hold the chains together and also the heme-group to the chain, are inaccessible for large molecules, e.g. enzymes which can split the bondings which keep the chain together; however, the bondings are accessible for small molecules, e.g. oxygen, which is transported within the body bonded to heme. This natural condition is shown in FIG. 1 sub A. The wound-up chains can be "unrolled" to straighter chains with the aid of denaturating agents, e.g. urea, alkali, oxygen, heat, organic solvents or combinations thereof. The four chains in a hemoglobin molecule will then be separated from each other which is shown in FIG. 1 sub B. Each such "unrolled" chain is now accessible for the attack of a proteolytic enzyme which can break down the bonding between amino acids in an amino acid chain, e.g. in hemoglobin. Different proteolytic eyzyme can break different such bondings but the result will always be that the length of the amino acid is shortened; this is shown in FIG. 1, C–E. Proteolytical enzymes can be obtained from organs from plants and animals and from microorganisms.

These proteolytic enzymes have the ability to break down the bondings between amino acids in an amino acid chain, e.g. hemoglobin. Different proteolytic enzymes break different such bondings but the result will in all cases be that the length of the amino acid chain is shortened; this is elucidated in FIG. 1C–E. The degree of decomposition is then determined by the nature of the enzyme, the time, the pH and the temperature at the interaction of the enzyme and the composition of the reaction products formed.

According to the present invention heme-protein is thus hydrolyzed with the aid of proteolytic enzymes so that superfluous amino acids are removed, whereas the natural heme-iron is retained at the amino acid to which it was originally bonded, as many amino acids in the neighbourhood of this bonding location being retained so that the desirable technical and physiological properties are obtained or maintained resp. in the product. After the hydrolysis the heme-protein can be separated into two main fractions, viz. one containing the major part of the heme-iron of the heme-protein having a heme-iron content which is up to 16 times greater than the heme-iron content of the original heme-protein, and a second fraction containing the major part of the amino acids of the heme-protein. The heme-iron-rich fraction can during the reaction be given greater molecular dimensions than the second fraction which can be used for separation of the fractions.

It is important that the iron is concentrated in the heme-iron-rich fraction without any addition of external iron, since the iron in the heme-protein and also in the heme-iron-rich fraction has a special natural form with an especially good resorbability in the human body. The fraction obtained is, due to its high content of this specific iron, a good iron source for use in foodstuffs and pharmaceuticals (therapeutical use).

There are a number of proteins which consist of amino acids and heme, in the present context called heme-proteins, among which hemoglobin, myoglobin, cytochrome, catalase and peroxidase are to be noted and occurring in the most cells of animal, vegetabilic and microbiological origin. The invention is applicable on all these heme-proteins but hemoglobin is the only material which seems to be of a practical importance.

The mixture (hydrolysate) resulting from the decomposition of a heme-protein according to the invention obtains other properties than the original protein. The water-solubility of the hydrolysate is normally independent of the pH, whereas the water-solubility of the starting protein commonly is dependent on the pH of the solution. The enzyme does not act on the heme-group per se in the process according to the invention.

The process defined above has hitherto not caused any greater difference as regards the molecular size between the heme-iron-containing and the non-heme-iron-containing fraction (1D–E). In an aggregation process the heme-iron-containing fraction can, however, be given such molecular dimensions that it can easily be separated from the fraction not containing heme-iron. This is shown in FIGS. 1F–G. Such an aggregation can be achieved either by adjustment of the pH or by concentration. If the pH is adjusted to 4.5 the heme-iron product will form aggregates so that it is precipitated and can be separated easily. If the concentration is increased by membrane filtration with the use of a tight membrane the heme-iron fraction aggregates continuously and does not pass through the membrane. If the pH is adjusted to about 7 before ultrafiltration and without a previous precipitation a more porous membrane can be used.

As has been shown above it has, according to the invention, been achieved that the protein rests to which the heme-group is bonded are given such a size that they can be used for separation of the heme-rich fraction (the heme-containing product). That such a size is achieved in the heme-rich protein rests seems to depend on the fact that either (a) the heme-iron-containing rests primarily have small dimensions but subsequently combine to the formation of greater aggregates due to hydrophobic interactions. These aggregates will then contain almost all of the heme-iron; or (b) part of the protein is left essentially unchanged during the enzymatic hydrolysis. These protein chains "take care of" the heme-group which during the proceeding hydrolysis of other protein chains no longer can be bonded to the lesser aggregates. Then a super-heme-protein would be formed, viz. a heme-protein with more than one heme-group per amino acid chain, due to hydrophobic interaction.

The following experiment has been made for the purpose to decide which of the mechanisms (a) and (b) is probable:

250 mgs of untreated hemoglobin and a heme-iron product prepared according to A in Example 1 were dissolved on the one hand in 25 mls of 10 M tris-buffer with pH 8.0 and on the other hand in 25 mls of the same buffer containing 2% of sodium lauryl sulphate (SLS).

All solutions were strongly coloured and transferred to dialysis tubes and dialyzed against the solvent (identically the same within and outsides of the tube). The dialysis tube prevents proteins from passing through the tube (to the solution outsides), but admits passage of smaller molecules, e.g. heme-peptides. SLS has the ability to stop hydrophobic interaction and thus subdivides larger molecular aggregates to separate molecules. During the dialysis passage of coloured material occurred only in the system wherein the heme-iron product was dissolved and dialyzed with tris-buffer containing SLS. In all other cases the colour (the heme) remained inside the tube wall. Special analysis of the coloured material which had passed the tube wall showed that this had the same proportions between iron and amino acids as the material within the tube. This experiment permits the conclusion that hydrophobic interaction causing aggregate formation of heme-containing peptides is the main mechanism (according to alternative a); this is elucidated in FIGS. 1F-G.

A continuing enzymatic hydrolysis of hemoglobin according to the invention thus seems to cause such a hydrophobic interaction between heme-containing hemoglobin fragments that these are assembled to aggregates which can be separated from material which does not contain heme instead of, as could be expected, being distributed in the hydrolysis and the rest fractions.

According to the invention it is thus possible by a suitable choice of denaturation method, reaction conditions for the enzymatic hydrolysis of heme-protein and separation method to prepare heme-iron products with an increased content of heme-iron, by removing the amino acids liberated during the hydrolysis; neither heme nor iron is required to be added from an external source.

A suitable starting material for the present process is whole blood from animals or red blood corpuscles which contain all hemoglobin in blood. The blood corpuscles are the part of the whole blood which remains when the blood plasma has been separated. For use in the present process the red blood corpuscles must be subdivided both when they are used as such or in the form of whole blood. The decomposition is simplest made by osmotic treatment in the presence of water; the blood corpuscles will burst when water is added and their content of hemoglobin is separated to the solution (hemolysis). The hemolysis is suitably made by adding 1-4 parts of water to whole blood or blood corpuscles.

The denaturation of the heme-protein is suitably made by the addition of alkali, preferably $Ca(OH)_2$ and above all NaOH or KOH, to a pH of 11, whereupon pH 11 is maintained for 30 minutes up to 8 hours; before the hydrolysis the pH is suitably decreased, e.g. with mineral acids, to pH 7-9 depending on the chosen enzyme. Denaturation can also be achieved by the addition of urea or acid or a solvent mixable with water. The hydrolysis can be made by adding a proteolytic enzyme to denaturated hemoglobin in a concentration of for instance 1-12% in water, preferably 4-8%. This enzyme can be of an animal origin, i.e. trypsin and chymotrypsin, or a plant enzyme, e.g. papain, bromelain and ficin, or of a microbial origin, suitably an enzyme from microorganisms which are permitted for foodstuff use, e.g. certain bacteria belonging to the genus Bacillus or fungi belonging to the genus Aspergillus. Such microbial enzymes are commercially available, for instance under the trade names Alcalase ® and Neutrase ® which are obtained from bacillus and have a strength of 6 and 1.5 Anson units/g resp. and they are permitted for use in foodstuffs. All the exemplified enzymes are prepared by a number of different manufacturers and for the present purpose they are equally usable under the condition that they are used in a similar manner. It will be necessary to use amounts of the different enzymes which give the same effect. A way to express the activity of proteolytic enzymes in so-called Anson units (cf. N. L. Davis and E. L. Smith, "Methods of Biochemical Analysis", Vol. II, page 215, Interscience Publishers, New York, 1955). An Anson unit is the amount of enzyme which is required for decomposition of a standard protein to a certain extent during a certain period of time. Commercial enzyme preparations usually contain 0.1-50 Anson units per gram depending on the degree of enrichment.

The enzymatic hydrolysis is suitably performed at a constant temperature, e.g. within the range 10°-80° C., suitably 25°-60° C., depending on the optimal temperature and stability of the chosen enzyme. The choice of temperature can also be determined on the basis of the desired reaction rate. A change of the temperature to low or high values, e.g. to lesser than 10° C. and higher than 80° C., can be used for a heavy decrease of the reaction velocity or a complete stopping of the reaction.

In the hydrolysis pH is another parameter which can be chosen depending on the pH optimum and pH stability of the chosen enzyme, e.g. in the range 4-11. For plant enzymes such as papain pH can be relatively low, e.g. 5, whereas for alkaline microbial proteases a higher value is suitably chosen, e.g. 9-10. The reaction velocity can also be governed with the aid of pH.

In hydrolysis of proteins carboxy groups are liberated which tend to decrease the pH of the reaction mixture. If the pH is allowed to decrease in this manner the pH decrease will continuously change the reaction velocity. If the reaction is started at or below the optimal pH of the enzyme the reaction velocity will gradually decrease, whereas when the starting pH is chosen above the optimal pH of the enzyme the reaction velocity will first increase until the pH optimum is reached, whereupon the velocity will gradually decrease. pH can also be kept constant during the reaction by continuous addition of alkali, suitably NaOH or KOH, preferably in an aqueous solution, the added amount of alkali per time unit also being a measure of the reaction velocity and the total added amount of alkali being a measure of the hydrolysis degree.

The hydrolysis products formed during the reaction will retard the reaction by its blocking action on the enzyme; accordingly, the hydrolysis products also govern the course of the reaction. If these hydrolysis products are allowed to remain in the reaction mixture they will alone or together with other parameters which govern the reaction such as the temperature and the pH influence the velocity of the reaction and the hydrolysis degree. Such conditions prevail in a simple reaction vessel in which the reactants are admixed and the reaction will proceed until it stops.

If the reaction is performed under such conditions that the hydrolysis products are continuously removed the reaction will on the other hand be influenced to a much lesser extent of these products; accordingly, the reaction can be governed to an essential extent as regards velocity and hydrolysis degree in other ways, e.g. with the aid of the temperature and the pH. The hydrolysis products can continuously be removed in several ways, preferably by ultrafiltration. Ultrafiltration is performed by pressing the reaction mixture against a porous membrane which is of such a nature that molecules up to a certain magnitude can pass through the membrane, whereas greater molecules are retained. By choosing a membrane with a suitable pore size it is possible to decide the greatest magnitude of the molecules which pass through the membrane. The properties of the material passing through the membrane as well as the properties of the material which does not pass through the membrane can, like the reaction velocity and the hydrolysis degree, be governed by a suitable choice of reaction and ultrafiltration parameters, such as temperature, pH, protein/enzyme ratio, membrane choice, pressure and circulation conditions, the volume of the reaction mixture, addition of alkali, etc.

Since the heme-iron content is the most interesting property of the final preparation in this context the reaction must be performed in such a manner that preferably amino acids and as little as possible of the heme-iron is removed. The properties of the heme-iron-containing fraction should further be adjusted so that it can be easily separated from the remainder of the material. This is achieved by a suitable choice of reaction conditions, above all the choice of the enzyme, the hydrolysis pH and the reaction time, precipitation or membrane filtration; the content of heme-iron can also be varied in this manner.

In the flow sheet below the invention is elucidated as described above. According to the route in alternative 1 only the heme-containing fraction can be precipitated at pH 4-5. According to alternative 2 only the heme-containing fraction can be concentrated by ultrafiltration. By combination of ultrafiltration and precipitation (alternative 3) also the heme-containing fraction can be concentrated.

The technical properties required in the present heme-iron product depend on the intended use. Below it will be shown only how to prepare a heme-iron-enriched preparation according to the invention with monitoring of the heme-iron enrichment. The product can be adapted to the required technical properties with the aid of the same measures as those used for the heme-iron enrichment described above but also other methods can be used which per se do not have any interaction on the heme-iron enrichment.

The invention is described in detail in the following examples.

EXAMPLE 1

Influence of enzyme and pH.

To each one of six batches (A-F) each containing 1000 gs of dark plasma containing 350 gs of protein, 14 gs of heme and 1.1 gs of iron 1000 gs of water were added under stirring for hemolysis of the blood corpuscles. Subsequently each of the batches A-F was admixed with further 3000 gs of water and so much 5 N aqueous NaOH that the pH was increased to 11.

After 1 hour at room temperature so much 1 M aqueous citric acid solution was added to batches A, C and E that the pH decreased to 9.0 and to batches B, D and F a sufficient quantity to make the pH 7.5. All batches were filtrated through paper filters. The temperatures in batches A-F were adjusted to 50° C. Batches A and B were then admixed with 3.5 gs of Alcalase ®, batches C and D with 14 gs Neutrase ® and batches E and F with 7 gs of papain. All these enzyme preparations, Alcalase ®, Neutrase ® and papain, were dissolved in 50 mls of 0.1M phosphate buffer of pH 8. The addition of the enzyme preparation started hydrolysis in all batches. During the hydrolysis the changes of pH were monitored with the aid of a pH-meter and 5 N aqueous NaOH were added in portions and with such a frequency that pH always was kept within the range 8.7-9 in batches A, C and E and within the range 7.2-7.8 in batches B, D and F. After 2 hours the hydrolysis velocity was decreased by decrease of the temperature to 10° C., whereupon batches A-F were admixed with so much of 3 M aqueous HCl that pH in all of the batches decreased to 4.5. In all batches a dark precipitation was formed which was removed by centrifugation and dried; nitrogen and iron analysis was then made on the dried precipitation. Already an ocular inspection of the precipitations and the solutions showed that there were differences as to the heme content. The results of the analysis are given in the following table.

| Batch | Enzyme | pH | Iron content (mg/g) | Degree of enrichment* |
|---|---|---|---|---|
| Dark plasma | | | | |
| A | Alcalase ® | 9.0 | 12.9 | 4.0 |
| B | " | 7.5 | 5.2 | 1.6 |
| C | Neutrase ® | 9.0 | 5.6 | 1.8 |
| D | " | 7.5 | 6.0 | 1.9 |
| E | Papain | 9.0 | 12.9 | 4.0 |
| F | " | 7.5 | 5.2 | 1.6 |

*Number of times enriched in relation to the iron content of the dark plasma

This example shows that the enriched iron preparation can be prepared by splitting hemoglobin with the aid of one iron-enriched fraction and one fraction containing amino acids which have been split off and that these fractions are separated by precipitation of the heme-iron-enriched fraction. The degree of enrichment at a constant hydrolysis time and temperature has been governed by adjustment of the pH and/or the choice of the enzyme. Alcalase ® as well as papain have thus given a considerably greater iron enrichment at pH 9.0 than at pH 7.5, whereas Neutrase ® gave essentially the same results at pH 9.0 and 7.5.

EXAMPLE 2

Membrane process

To each one of two batches (A and B), each amounting to 5 kgs of dark plasma containing 1600 gs of protein 5 kgs of water were added for hemolysis of the blood corpuscles, whereupon denaturation was performed by alkali treatment at pH 11 and filtration analogous with Example 1. Subsequently further 35 kgs of water were added so that each batch weighed totally 45 kgs, whereupon pH was adjusted to 9.0 with 2 M aqueous HCl. After adjustment of the temperature to 50° C. in a jacketed steel vessel the both batches were admixed with 22.5 gs of Alcalase ®, dissolved in 500 mls of 0.1 M aqueous phosphate buffer of pH 8.0 for starting the hydrolysis reaction. During the reaction pH was kept in the range 8.8-9.2 in the manner described in Example 1. The hydrolysis was performed at an essentially constant pH by addition of aqueous sodium hydroxide, at first during a short hydrolysis period in the jacketed vessel, this prehydrolysis period being 21 minutes for batch A and 7.5 minutes for batch B. Then the hydrolysis was performed under ultrafiltration which for batch A lasted for 64 minutes and for batch B for 45 minutes. The ultrafiltration in which the iron-enriched fraction was separated from the amino acid fraction was performed in membranes of the type "hollow fibre" with a nominal separation degree of 10,000 dalton for batch A and 7000 dalton for batch B in the manner more closely described in Example 3. The treatment was in both cases stopped when 3.0 moles of NaOH had been added. At that time 5 liters of each batch remained, viz. 11% of the original volume. In both cases the residue was dried and analyzed for iron. The results are given in the following table.

| Batch | Ultrafiltration (Dalton) | Iron (mg/g) | Enrichment degree |
|---|---|---|---|
| Starting material | — | 2.2 | 1 |
| A | 10,000 | 5.2 | 2.4 |
| B | 7,000 | 8.8 | 4.4 |

The enrichment degre for iron can thus be governed with the aid of the porosity of the membrane.

EXAMPLE 3

Membrane process

Three batches (A–C) each consisting of 5000 gs of dark plasma containing about 1750 gs hemoglobin, 70 gs heme and 5.5 gs of iron were hemolyzed and denaturated as described in Example 1.

To batches A and B 1 M aqueous citric acid was added for decrease of the pH to 9.0 and to batch C 1 M aqueous citric acid was added for decrease of the pH to 7.5. All of the batches were adjusted to 54° C., whereupon enzyme was added. To each one of the batches A and B 18.6 gs of Alcalase ® were added, dissolved in 400 mls of 0.1 M aqueous phosphate buffer filtrated through paper filter and to batch C 74.4 gs of Neutrase ® in 400 mls of 0.1 M aqueous phosphate buffer at pH 7.5 was added, likewise with previous filtration; this started hydrolysis. pH was kept constant between 8.7 and 9.3 as regards the batches A and B and between 7.2 and 7.8 for batch C as described in Example 1. The reaction velocities in batches A, B and C were decreased after 20 minutes, 105 minutes and 210 minutes resp. by decrease of the temperature to about 40° C. (for all batches A–C), 2 M aqueous HCl also being added to batch B for decrease of the pH to 7.6. Ultrafiltration was then immediately started and the temperature was slowly decreased to the ambient temperature (about 20° C.). The ultrafiltration was in all cases performed with a membrane of the type "hollow fibre" with a separation limit (nominal molecular weight exclusion limit) of 50,000 dalton and with an active surface of 2.46 m². The pressure before the membrane was 100 kPa and after the membrane 70 kPa. The flow of the permeate was determined to 90 l/m².h, viz. the part of the solution which passed through the membrane. When about 5 liters of solution remained water was added in two portions, each consisting of 8 liters, for the purpose of further removing split-off amino acids. Finally, the remaining solution was concentrated by evaporation to about 3.5 liters. The obtained concentrates for batches A–C were dried and weighed, whereupon a nitrogen and iron analysis was performed. The results are given in the following table.

| Sample | Enzyme | Hydrolysis pH | Filtration pH | Time (min) | Iron (mg/g) | Enrichment degree |
|---|---|---|---|---|---|---|
| Dark plasma | — | — | — | — | 3.3 | 1.0 |
| A | Alcalase ® | 9.0 | 9.0 | 20 | 10.4 | 3.2 |
| B | Alcalase ® | 9.0 | 7.6 | 105 | 18.8 | 5.7 |
| C | Neutrase ® | 7.5 | 7.5 | 210 | 12.2 | 3.7 |

The results show that an enriched heme-iron preparation can be prepared by hydrolyzation of hemoglobin with an enzyme to the formation of an iron-enriched fraction and a second fraction containing split-off amino acids and by separating these fractions by ultrafiltration with the use of a membrane with a separating degree of 50,000 dalton and that a lower filtration pH is favourable for the enrichment degree.

The yield of heme-iron-enriched fraction was shown to be greater when the pH at the ultrafiltration was 7 instead of 9. By this adjustment of the pH before the ultrafiltration it is possible to use a more porous membrane than could be expected on the basis of the molecular weight ratios for hemoglobin and heme-iron-enriched (heme-enriched) fraction. In this manner the ultrafiltration will be more rapid. It can also be seen that the heme-iron enrichment can be governed by the choice of hydrolysis time, the same enzyme and the same pH being used, or by the choice of enzyme.

EXAMPLE 4

Pretreatment and hydrolysis av dark plasma were performed analogous with Example 3, the pH during the hydrolysis being kept at 9. Ultrafiltration was performed in a first case (A) with a membrane with the separation degree of 10,000 dalton and in a second case (B) first through a membrane with the separation degree of 50,000 dalton followed of filtration through a membrane with the separation degree of 10,000 dalton. In case B relatively more heme-iron passed the membrane with the separation degree of 50,000 dalton, since the pH at the ultrafiltration was 9, as compared with Example 3, wherein pH was 7. The heme-iron fraction from the filtrate in case B could be concentrated by ultrafiltration of the first filtrate once more but through a membrane with the separation degree of 10,000 dalton. In both cases (A, B) the material was recovered when 5 liters remained, whereupon pH in the both cases was decreased to 4.5 by the addition of hydrochloric acid. Precipitations were obtained which were recovered, dried, weighed and analyzed as to the iron content.

The results are shown in the following table.

| Sample | Iron (mg/g) | Enrichment degree |
|---|---|---|
| Dark plasma | 1.8 | 1.0 |
| Precipitation A | 19.5 | 6.9 |
| Precipitation B | 46.1 | 16.5 |

This example shows that the enrichment degree can be governed by different combinations of ultrafiltration and precipitation. The materials (precipitations A and B) prepared according to this example thus consist of 1.95 and 4.6% of iron resp. which corresponds to 22 and 54% heme (iron×11.64=heme); thus they contain 78 and 46% resp. of other materials which mainly consist of amino acids.

The examples show that heme-iron preparations can be prepared by enzymatic hydrolysis of hemoglobin to the formation of one heme-iron-enriched amino acid fraction and one amino acid fraction without heme-iron and that these two fractions can be separated, e.g. by precipitation of the heme-iron-enriched fraction or by ultrafiltration or by a combination of these methods. The heme-iron-enriched fraction still contains amino acids which play an important role for the transport and resorption of the heme-iron. The yield of iron, calculated on the iron content of the original dark plasma, was about 80% in all of the examples.

The most suitable specific form for the preparation of the present heme-iron-enriched amino acid preparation depends on its use. For achieving the best heme-iron enrichment the specific form according to Example 1B is most suitable when working without membrane technique, with the use of membrane technique the specific form according to Example 3B is most suitable and the combination of membrane technique and precipitation is most suitable according to the specific form in Example 4B.

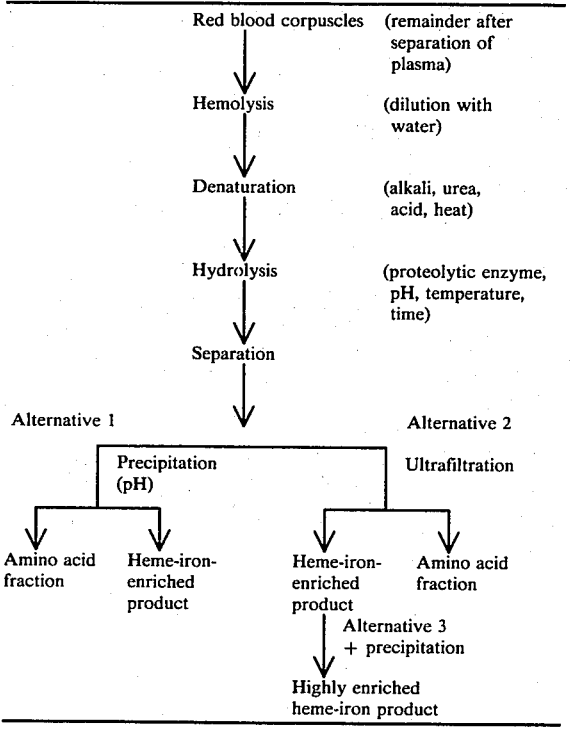

Flow sheet for alternative processes for the preparation of heme-iron-enriched preparations.

I claim:

1. Heme-iron-enriched amino acid product prepared from heme-proteins, wherein the iron content of the preparation consists solely of the porphyrin iron of the original heme-protein which is bonded as heme to amino acid chains which are shorter than the amino acid chains in the original heme-protein, but which are aggregated into units having larger dimensions than the separate, short, heme-iron-containing amino acid chains.

2. Amino acid preparation according to claim 1, which is comprised by a constant ratio between heme and iron and by a porphyrin heme-iron content of at least 0.5% and at the most 5%, calculated as the iron which is bonded to porphyrin.

3. A process for the preparation of heme-iron-enriched amino acid preparations from heme-proteins, wherein the heme-protein is first hemolyzed and denaturated and subsequently split up with the aid of proteolytic enzymes and forming one heme-iron-enriched fraction and one fraction which does not contain heme-iron and recovering the heme-iron-enriched fraction by separation and stabilizing it by heat treatment and dewatering.

4. A process according to claim 3, wherein the enzyme is obtained from preparations containing proteolytic enzymes selected from the group consisting of animals, plants, microorganisms or fungi.

5. A process according to claim 3 or 4, wherein the hydrolysis is conducted at the pH range of 4–11.

6. A process according to claim 5 wherein the hydrolysis is performed at a temperature of 10°–80° C.

7. A process according to claim 6, wherein the heme-iron-enriched fraction is separated from the amino acid-enriched fraction by precipitation means at a pH of 4–5 or by ultrafiltration.

8. A process according to claim 7, which comprises conducting the ultrafiltration at a pH of 5–9.

9. A process according to claim 7 wherein the separation is performed with the use of a membrane which has a separation degree of 10000–50,000 dalton or with a combination of membranes with a separation degree of 1000–50,000 dalton.

10. A process according to claim 7 which comprises separating the heme-iron-enriched fraction from the amino acid-enriched fraction by a combination of ultrafiltration and precipitation.

11. A process according to claim 9 which comprises separating the heme-iron-enriched fraction from the amino acid-enriched fraction by a combination of ultrafiltration and precipitation.

12. A process according to claim 8, wherein the separation is performed with the use of a membrane which has a separation degree of 1000–50,000 dalton or with a combination of membranes with a separation degree of 1000–50,000 dalton.

* * * * *